(12) United States Patent
Oscarsson et al.

(10) Patent No.: US 10,125,199 B2
(45) Date of Patent: Nov. 13, 2018

(54) MANUFACTURE OF MAGNETIC PARTICLES

(71) Applicant: Lab-on-a-bead AB, Lycke (SE)

(72) Inventors: Sven Oscarsson, Uppsala (SE); Kristofer Eriksson, Strängnäs (SE); Peter Svedlindh, Uppsala (SE)

(73) Assignee: Lab-on-a-bead AB, Lycke (SE)

( * ) Notice: Subject to any disclaimer, the term of this patent is extended or adjusted under 35 U.S.C. 154(b) by 21 days.

(21) Appl. No.: 15/064,661

(22) Filed: Mar. 9, 2016

(65) Prior Publication Data

US 2016/0185880 A1 Jun. 30, 2016

Related U.S. Application Data

(63) Continuation of application No. PCT/SE2014/051034, filed on Sep. 9, 2014.

(30) Foreign Application Priority Data

Sep. 9, 2013 (SE) .................................. 1351038

(51) Int. Cl.
| | | |
|---|---|---|
| C08B 37/00 | (2006.01) | |
| B01J 20/32 | (2006.01) | |
| B01J 20/285 | (2006.01) | |
| B01J 20/28 | (2006.01) | |
| B01J 20/286 | (2006.01) | |
| B01J 20/24 | (2006.01) | |
| G01N 33/543 | (2006.01) | |
| G01N 33/548 | (2006.01) | |
| B01D 15/38 | (2006.01) | |

(52) U.S. Cl.
CPC .......... *C08B 37/0039* (2013.01); *B01J 20/24* (2013.01); *B01J 20/285* (2013.01); *B01J 20/286* (2013.01); *B01J 20/28009* (2013.01); *B01J 20/28016* (2013.01); *B01J 20/321* (2013.01); *B01J 20/3204* (2013.01); *B01J 20/3212* (2013.01); *B01J 20/3217* (2013.01); *B01J 20/3242* (2013.01); *B01J 20/3265* (2013.01); *G01N 33/548* (2013.01); *G01N 33/5434* (2013.01); *B01D 15/3804* (2013.01); *B01D 15/3885* (2013.01)

(58) Field of Classification Search
CPC ............. C08B 37/0039; B01J 20/28009; B01J 20/28016; B01J 20/3212; B01J 20/3242; B01J 20/285
USPC ...................................................... 536/123.1
See application file for complete search history.

(56) References Cited

U.S. PATENT DOCUMENTS

| | | | |
|---|---|---|---|
| 4,123,396 A | 10/1978 | Rembaum et al. | |
| 4,141,687 A | 2/1979 | Forrest et al. | |
| 4,157,323 A | 6/1979 | Yen et al. | |
| 4,452,773 A | 6/1984 | Molday | |
| 4,672,040 A | 6/1987 | Josephson | |
| 5,200,084 A | 4/1993 | Liberti et al. | |
| 5,691,208 A | 11/1997 | Miltenyi et al. | |
| 8,071,395 B2 | 12/2011 | Davis et al. | |
| 2005/0196856 A1 | 9/2005 | Harrold et al. | |
| 2006/0189797 A1* | 8/2006 | Songe ................ | B01D 15/3828 530/412 |
| 2006/0216751 A1 | 9/2006 | Boschetti et al. | |
| 2007/0178604 A1* | 8/2007 | Watkins ............. | G01N 33/6893 436/500 |
| 2010/0047878 A1 | 2/2010 | Lee | |
| 2012/0037840 A1 | 2/2012 | Stucky et al. | |
| 2013/0197195 A1 | 8/2013 | Oscarsson et al. | |

FOREIGN PATENT DOCUMENTS

| | | |
|---|---|---|
| CN | 102703411 A | 10/2012 |
| JP | S61-283624 A | 12/1986 |
| JP | 2004-528550 A | 9/2004 |
| JP | 2005-516077 A | 6/2005 |
| JP | 2008-538112 A | 10/2008 |
| WO | 1995/003356 A1 | 2/1995 |
| WO | 2002/075309 A1 | 9/2002 |
| WO | 2003/004151 A1 | 1/2003 |
| WO | 2006/017428 A2 | 2/2006 |
| WO | 2009/131526 A1 | 10/2009 |
| WO | 2009/151490 A2 | 12/2009 |
| WO | 2012/013693 A1 | 2/2012 |
| WO | 2013/187831 A1 | 12/2013 |

OTHER PUBLICATIONS

International Search Report for co-pending International Application No. PCT/SE2014/051034 dated Dec. 17, 2014.

Written Opinion of the International Search Authority for co-pending International Application No. PCT/SE2014/051034 dated Dec. 17, 2014.

International Preliminary Report on Patentability for co-pending International Application No. PCT/SE2014/051034 dated Jul. 6, 2016.

International Search Report for co-pending International Application No. PCT/SE2014/051036 dated Dec. 17, 2014.

Written Opinion of the International Search Authority for co-pending International Application No. PCT/SE2014/051036 dated Dec. 16, 2014.

International Preliminary Report on Patentability for co-pending International Application No. PCT/SE2014/051036 dated Dec. 16, 2014.

(Continued)

*Primary Examiner* — Yih-Horng Shiao
(74) *Attorney, Agent, or Firm* — Renner, Otto, Boisselle & Sklar, LLP (57) ABSTRACT

A method for the production of particles by reacting functional groups on the surface of non-magnetic porous particles with functional groups on the surface of magnetic particles to form a covalent bond, to obtain particles supplemented with magnetic particles covalently bound to the outer part of said particles. Advantages include an increased binding capacity.

15 Claims, 3 Drawing Sheets

(56) References Cited

OTHER PUBLICATIONS

International Search Report for co-pending International Application No. PCT/SE2014/051037 dated Dec. 19, 2014.
Written Opinion of the International Search Authority for co-pending International Application No. PCT/SE2014/051037 dated Dec. 19, 2014.
International Preliminary Report on Patentability for co-pending International Application No. PCT/SE2014/051037 dated Dec. 18, 2014.
Safarik et al., "Large-scale separation of magnetic bioaffinity adsorbents", Biotechnology Letters 23, 2001, pp. 1953-1956.
Berensmeier, "Magnetic particles for the separation and purification of nucleic acids", Applied Microbiology and Biotechnology, vol. 73, Issue 3, Dec. 2006, pp. 495-504.
English translation of Office Action received in corresponding Chinese Application No. 2014800590596 dated Apr. 7, 2017.
Extended European Search Report for corresponding European Application No. 17208461.8 dated Mar. 7, 2018.
Office Action issued in co-pending U.S. Appl. No. 15/064,720, dated Feb. 22, 2018.
Safarik et al., "Magnetic techniques for the isolation and purification of proteins and peptides", BioMagnetic Research and Technology, 2004, 2:7, pp. 1-17.
English Translation of Office Action in the corresponding Japanese Application No. 2016-540851 dated May 23, 2018.
Nixon et al., "Preparation and Characterizataion of Novel Magnetite-Coated Ion-Exchange Particles", Chem. Mater., vol. 4, No. 1, 1992, pp. 117-121.

* cited by examiner

MANUFACTURE OF MAGNETIC PARTICLES

This application is the continuation of international Application No. PCT/SE2014/051034, which claims priority to Swedish patent application SE 1351038-3, filed 9 Sep. 2013, the entire content of which is hereby incorporated by reference.

TECHNICAL FIELD

The present description relates generally to manufacture of magnetic particles suitable for the separation and analysis of molecules and cells, comprising clusters where a non-magnetic porous particle is supplemented with magnetic particles.

BACKGROUND

Techniques for the separation and analysis of biomolecules and cells are of crucial importance in many technical fields, including but not limited to biopharmacy, biotechnology, food technology, analytical chemistry, medicinal chemistry, and water purification. For instance chromatographic methods based on bioaffinity have been used for more than 50 years. One important bioaffinity system is the immobilized Protein A by which immunoglobulins will interact biospecifically. This makes it possible to isolate monoclonal antibodies in a very efficient fashion.

The most frequently used separation technique today is a chromatographic technique where the separation media is packed in a cylinder and connected to a chromatographic system which makes it possible to isolate the molecules of interest. One of several disadvantages with this technique is the process time. Not only does the separation itself take considerable time, it is also time-consuming to set up the chromatographic system. The instruments and the equipment are expensive and require time to set up. Further, expert knowledge and experience is needed to be able to handle the system and to evaluate the results.

Alternatives exist and the use of magnetic particles is one of them.

U.S. Pat. No. 6,623,655 discloses a method for the preparation of a metal chelating compound.

Zhao at al. in Lab Chip, 2009, 9, 2981-2986 describe a technology to manufacture particles with a compartment intended for cells and a compartment with magnetic nanoparticles.

U.S. Pat. No. 4,438,179, describes a polymer particle having magnetic particles bound to its surface. The magnetic material is bonded with a layer of a bonding polymer comprising functional groups which functional groups are ionic or capable of forming a metal chelate or complex. Alternatively the magnetic material is bonded by a polyethylene glycol and/or a polypropylene glycol.

WO 2012/015891 discloses a particle which may be porous with smaller inorganic particles on its surface. The particle is presented as a toner particle for printers.

GB 1577930 discloses adsorptive particles and magnetic particles embedded in a porous polymer matrix. The porosity of the matrix is such as to allow only molecules up to a certain molecular weight to penetrate into the interstices of the matrix, so that the product selectively adsorbs dissolved substances out of solution. The compounded materials, especially in the form of pearls, are especially useful in the food industry e.g. to separate unwanted trace flavors from various food products or to recover useful materials such as vitamins from various products. Particular applications include removal of bitter isohumulones from concentrated yeast extracts; and recovery of riboflavin from whey. The particles containing the selectively adsorbed substance are easily separated from the medium due to their magnetic properties and thus overcome separation problems encountered with prior art adsorptive materials of this type. The adsorptive particles may be e.g., of carbon, $Al_2O_3$, silica gel, activated Mg silicate, clays, etc. The magnetic particles may be e.g., of magnetite, gamma-$Fe_2O_3$, ferrites, etc. The porous matrix may be e.g. PVC, polyacrylamide (optionally crosslinked with epichlorhydrin) phenolic resins, nylon-6, 6 crosslinked with HCHO, etc.

U.S. Pat. No. 8,518,265 concerns a functional powder comprising magnetic particles, and hydrophobic groups and hydrophilic groups provided on the surfaces of the magnetic particles; where the number (M) of the hydrophobic groups and the number (N) of the hydrophilic groups satisfy the condition of M/N is 0.2-0.8. An independent claim is included for water treatment method (for example treatment of wastewater such as industrial wastewater) involving dispersing the functional powder in water containing impurities so that the impurities are adsorbed on the surface of the powder, and removing the functional powder having adsorbed the impurities from the water by use of magnetic force.

Porous polymer particles comprising magnetic material are used today for purposes such as purification of various substances etc. Although such particles are successfully used in commercial applications, there remains room for improvement. In prior art particles, the magnetic material in the particles occupies a significant part of the space in the particles which could be used for purification or analysis.

Thus there is a need in the prior art to provide particles for purification purposes with increased loading capacity. There is also a need for a simple and robust method both for manufacture and when using the particles for various purposes.

SUMMARY

It is an object of the invention to alleviate at least some of the disadvantages of the prior art and to provide an improved material for separation and/or analysis as well as a manufacturing method for the material.

In a first aspect there is provided a method for the production of particles (P), said method comprising the steps of:

a. providing
   non-magnetic porous particles (Pp) having an exterior surface, pores and a connected interior surface defined by said pores, the porous particles (Pp) comprising at least one polymer, the porous particles (Pp) comprising at least one type of functional groups on said exterior and interior surfaces, and
   magnetic particles (Mp) comprising at least one type of functional groups on their surface wherein the smallest diameter of at least 95 wt % of all magnetic particles (Mp) is larger than the average diameter of the pores of the porous particles (Pp), and b. reacting functional groups on the surface of the non-magnetic porous particle (Pp), with functional groups on the surface of the magnetic particles (Mp) to form a covalent bond, to obtain particles (P) supplemented with magnetic particles (Mp) covalently bound to at least one selected from the interior surface and the exterior surface of the porous particles (Pp), wherein all of the at least one type of functional groups on the surface of the magnetic particles (Mp) have not reacted to form covalent bonds with the at least one type of functional groups on the exterior and interior surfaces of the porous particles (Pp) so that a fraction of the at least one type of functional groups remain available on at least one selected from the magnetic particles (Mp) and the porous particles (Pp).

In a second aspect there is provided a particle (P) comprising a non-magnetic porous particle (Pp) having an exterior surface, pores and an interior surface defined by said pores, the porous particles (Pp) comprising at least one polymer, said particle (Pp) having at least one magnetic particle (Mp) covalently bound thereto wherein the smallest diameter of at least 95 wt % of all magnetic particles (Mp) is larger than the average diameter of the pores of the porous particles (Pp).

Particles (P) according to aspects and embodiments described herein have an increased binding capacity compared to known magnetic particles. The binding capacity is maintained and/or even improved by formation of a particle (P) supplemented with magnetic particles (Mp) on which ligands can also be immobilized leaving the main part of the inner volume of the porous particle (Pp) unaffected and available to adsorption and binding reactions with the component to be separated. Since a porous particle (Pp) has most of its specific surface area on the interior, the reaction and/or adsorption capacity will be maintained if the magnetic particles (Mp) are not too small and not blocking the pores of the porous particle (Pp).

A further advantage is that all steps during the preparation of the particles (P) are easy to perform even in aqueous solutions and at moderate temperatures (i.e. at about 20-60° C.).

Another advantage is that the covalent bonds formed during the reactions involving the groups on the surface and inside the porous particle (Pp) are stable, even for single point attached molecules.

An important advantage is that the magnetic particles are strongly bound to the porous particles, which makes it possible to subject the particles to high flow velocities. The improved strength of the particles maintains the integrity of the particles, and also makes them adhere strongly to magnetic surfaces, making it possible to perform magnetic separation also in flowing media.

Yet another advantage is that the method can be performed with very few steps. The method is easier to perform compared to methods according to the prior art.

It is an advantage that the binding capacity of the particles (P) is increased for instance because the magnetic particles (Mp) can also contribute to the binding capacity due to their functional groups on the surface. Functional groups which have not participated in creating the covalent bonds between the magnetic particles (Mp) and the porous particle (Pp) are suitably utilized to improve the binding capacity, either as such or by further reaction with other molecules.

BRIEF DESCRIPTION OF THE DRAWINGS

Aspects and embodiments will be described with reference to the following drawings in which.

DETAILED DESCRIPTION

Before the describing various aspects and embodiments in detail, it is to be understood that this description is not limited to particular compounds, configurations, method steps, substrates, and materials disclosed herein as such compounds, configurations, method steps, substrates, and materials may vary somewhat. It is also to be understood that the terminology employed herein is used for the purpose of describing particular embodiments only and is not intended to be limiting since the scope of the present embodiments is limited only by the appended claims and equivalents thereof.

It must be noted that, as used in this specification and the appended claims, the singular forms "a", "an" and "the" include plural referents unless the context clearly dictates otherwise.

Also, the term "about" is used to indicate a deviation of ±10%, and most preferably ±5% of the numeric values, where applicable.

If nothing else is defined, the scientific terminology including any terms used herein are intended to have the meanings commonly understood by those of skill in the art to which this disclosure pertains.

As used throughout the description and the claims, the diameter of a sphere is any straight line that passes through the center of the sphere and whose endpoints lie on the sphere.

The inventors have carried out extensive research and found that the particles (P) defined in the claims are easy to form with high yield and easy to separate. The capacity to bind biomolecules to the cluster and to isolate biomolecules from the cluster was found to be higher than any published data for corresponding particles according to the state of the art.

The formed particles (P) according to an embodiment are magnetic and easy to use in processes for separation of biomolecules. Their usefulness is equally great in small scale and large scale applications. The particles together with immobilized molecules and/or cells are easily separated using external magnets. As the magnetic particles (Mp) give added density to the particles (P) the separation can be aided by centrifugation or by static settling using gravity. Density-based separation can be used as a pre-separation step and/or as part of the magnetic separation.

In a first aspect there is provided a method for the production of particles (P), said method comprising the steps of:

a. providing
   non-magnetic porous particles (Pp) having an exterior surface, pores and a connected interior surface defined by said pores, the porous particles (Pp) comprising at least one polymer, the porous particles (Pp) comprising at least one type of functional groups on said exterior and interior surfaces, and
   magnetic particles (Mp) comprising at least one type of functional groups on their surface wherein the smallest diameter of at least 95 wt % of all magnetic particles (Mp) is larger than the average diameter of the pores of the porous particles (Pp), and
b. reacting functional groups on the surface of the non-magnetic porous particle (Pp), with functional groups on the surface of the magnetic particles (Mp) to form a covalent bond,
to obtain particles (P) supplemented with magnetic particles (Mp) covalently bound to at least one selected from the interior surface and the exterior surface of the porous particles (Pp),
wherein all of the at least one type of functional groups on the surface of the magnetic particles (Mp) have not reacted to form covalent bonds with the at least one type of functional groups on the exterior and interior surfaces of the porous particles (Pp) so that a fraction of the at least one type of functional groups remain available on at least one selected from the magnetic particles (Mp) and the porous particles (Pp).

In one embodiment the smallest diameter of at least 95 wt % of all magnetic particles (Mp) is larger than the largest diameter of at least 95% of all pores of the porous particles (Pp).

The smallest diameter of at least 95 wt % of all magnetic particles (Mp) describes the smallest of all possible diameters of at least 95 wt % of all magnetic particles (Mp). Weight percentage and not number is used to reduce the relative weight of very small particles.

The average diameter of the pores of the porous particles (Pp) is measured and defined as the apparent pore dimensions as further detailed in Hagel, Östberg, Andersson in Journal of Chromatography A, Volume 743, issue 1, 30 Aug. 1996, pages 33-42. There is also data for some commercially available polymers. For instance the average (or apparent) pore diameter in 6% agarose is 24 nm.

When the smallest diameter of almost all (at least 95 wt %) of all magnetic particles (Mp) is larger than the average diameter of the pores of the porous particles (Pp), the magnetic particles can enter the porous particles (Pp) to some extent, but not to a so large extent that the magnetic particles (Mp) block the capacity of the porous particles (Pp). By allowing the magnetic particles (Mp) to enter the porous particles (Pp) to some extent the total binding capacity of the particles (P) can actually increase, since the magnetic particles (Mp) have available functional groups on their surface which can be utilized to increase the binding capacity either directly or by further reaction to bind other molecules. By allowing a fraction of the magnetic particles (Mp) to enter the load of magnetic material is increased in the particles, which makes the particles (P) more useful for separation, since it is easier to separate them if they have more magnetic material in them.

For many applications, in particular for separation a high magnetic moment is desired for the particle. Also the binding capacity of the particle P should be high. This is solved so that the magnetic particles (Mp) are possible to derivatize with functional groups so that they contribute to the total binding capacity of the particle (P). Both the binding capacity of the particle (P) and the magnetic moment is maximized by allowing some magnetic particles (Mp) to enter the porous particle (Pp) and by derivatizing the magnetic particles (Mp) with functional groups that contribute to the total binding capacity of the particle (P).

In one embodiment the magnetic particles (Mp) are 20 nm or larger. In one embodiment the magnetic particles (Mp) are 4 μm or smaller. In an alternative embodiment the magnetic particles (Mp) are 100 nm or smaller. In one embodiment a stable colloid of magnetic particles (Mp) is utilized during the manufacturing process. The diameter of individual magnetic particles (Mp) is used, if the magnetic particles (Mp) form clusters the largest diameter of the entire cluster can be considerably larger.

It is conceived that even if the manufacturing processes are satisfactory there may be a few particles which are smaller or larger than the intended size in a practical manufacturing process.

In an alternative embodiment, the smallest diameter of the magnetic particles (Mp) is equal or smaller than the average diameter of the pores of the porous particle (Pp). In this embodiment, at least a portion of the magnetic particles will enter into the pores of the porous particle. By choosing the size of the magnetic elements in relation to the pore size, the magnetic load can be adapted as desired.

The smallest diameter of the magnetic particles (Mp) is larger than the average diameter (apparent diameter) of the pores of the porous particle (Pp). It is intended that the smallest diameter of the magnetic particles (Mp) means the smallest diameter of essentially all (at least 95 wt %) magnetic particles (Mp), where smallest diameter is measured in a dimension where the size of the particle is smallest. In such an alternative embodiment essentially all magnetic particles (Mp) are too large to enter in an average pore of the porous particle. It is conceived that the pore size can vary and will have a certain size distribution, and some pores are accessible for the magnetic particles (Mp) in such an embodiment.

In yet an alternative embodiment the smallest diameter of the magnetic particles (Mp) is larger than the diameter of all pores of the porous particle (Pp). In such an embodiment no pores are accessible for the magnetic particles (Mp).

For some diagnostic applications it is desired that magnetic particles (Mp) are only on the exterior surface of the porous particles (Pp).

According to one embodiment the porous particles (Pp) are essentially spherical, however also other shapes are encompassed and the porous particles (Pp) are not limited to any specific shape. All shapes are encompassed within the scope of the embodiments presented herein. The same applies to the magnetic particles (Mp).

For a spherical or an essentially spherical particle the diameter is easy to determine according to the usual definition. For a perfectly spherical particle the smallest and the largest diameter are the same. However for irregularly shaped particles, i.e. non-spherical particles, the diameter can be measured in many different directions from one point on the surface through the center of mass to another point on the surface. One such diameter will be the smallest for an irregular particle and one such diameter will be the largest. The center of mass for a sphere is the center of the sphere, provided that the sphere is uniform. For a sphere the diameter should pass through the center of the sphere.

In one embodiment the porous particle (Pp) comprises a material selected from the group consisting of agarose, silica, cellulose, poly vinyl alcohols, polyethylene glycols, polystyrene, dextran, acrylates and derivatives thereof.

In one embodiment the magnetic particles (Mp) have a density which is higher than the density of the non-magnetic porous particle (Pp).

In one embodiment the at least one type of functional groups on the exterior and interior surfaces the porous particle (Pp) are selected from the group consisting of —SH, —S—S-pyridin, —COOH, —NH$_2$, —CHO, —OH, phenol, anhydride, epoxy, S-Au, and amide.

In one embodiment the functional groups on the exterior and interior surfaces of the porous particle (Pp) include at least one group which is the result of a reaction with at least one compound selected from the group consisting of divinylsulfone, benzoquinone, imidazole, periodate, trichloro-S-triazine, tosylates, diazonium, isourea salts, carbodiimides, hydrazine, epichlorohydrin, glutaraldehyde, cyanogenbromide, bisepoxiranes, carbonyldiimidazole, N-hydroxysuccinimide, silanes and derivatives thereof.

In one embodiment the functional groups on the magnetic particles (Mp) include at least one selected from the group consisting of —SH, —S—S—pyridin, —COOH, —NH$_2$, —CHO, —OH, phenol, anhydride, epoxy, S-Au, and amide.

In one embodiment at least one selected from the at least one type of functional groups on the exterior and interior surfaces the porous particle (Pp) and the at least one type of functional groups on the surface of the magnetic particles (Mp) comprise complex binding groups. In one embodiment the complex binding groups is at least one selected from the group consisting of IDA (Iminodiacetate) and derivatives thereof, TED (tris(carboxymethyl) ethylenediamine) and derivatives thereof, CM-Asp (Carboxymethylated aspartic acid) and derivatives thereof, NTA (nitrilotriacetic acid) and derivatives thereof, TREN (tris(2-aminoethyl) amine) and derivatives thereof, DPA (dipicolylamine) and derivatives thereof, C6-S gel (hexylsulfido groups) and derivatives thereof, EDTA (Ethylenediaminetetraacetate) and derivatives thereof. These complex binding structures can bind for instance metal ions which in turn can interact with a peptide chain comprising histidine. If antibodies comprising a histidine chain or tag are to be purified such groups are suitable to use.

In one embodiment at least one selected from the at least one type of functional groups on the exterior and interior surfaces the porous particle (Pp) and the at least one type of functional groups on the surface of the magnetic particles (Mp) comprise hydrophobic groups. In one embodiment the hydrophobic groups are at least one selected from the group consisting of $C_nH_m$ (1≤n≤20 4≤m≤42), phenol and derivatives thereof, thiophenol and derivatives thereof, and mercaptopyridine and derivatives thereof. Such hydrophobic groups are suitable if the particles are to be used in applications similar to hydrophobic chromatography. $C_nH_m$ (1≤n≤20 4≤m≤42) is a general formula for many different organic compounds including but not limited to alkanes $C_nH_{2n+2}$.

In one embodiment at least one selected from the at least one type of functional groups on the exterior and interior surfaces the porous particle (Pp) and the at least one type of functional groups on the surface of the magnetic particles (Mp) comprise at least one selected from the group consisting of aminoethyl, diethylaminethyl, quaternary aminoethyl, carboxyethyl, phosphor and sulphopropyl and derivatives thereof.

In one embodiment the magnetic particles (Mp) comprise at least one polymer.

In one embodiment the unreacted fraction of the at least one type of functional groups on the surface of the magnetic particles (Mp) which remains is reacted to facilitate subsequent binding of molecules to the magnetic particles (Mp). The functional groups which have not been reacted to form covalent bonds to the porous particles (Pp) are suitably utilized to increase the binding capacity of the particles (P) for selected substances by offering binding to the magnetic particles (Mp) as well as the porous particles (Pp). In one embodiment all functional groups on the porous particles (Pp) are also not reacted so that they can be utilized to increase the total binding capacity of the particle (P) as well.

In one embodiment at least 25% of the functional groups remain unreacted. In an alternative embodiment at least 50% of the functional groups remain unreacted. In yet another alternative embodiment at least 75% of the functional groups remain unreacted.

In one embodiment the functional groups on the surface of the magnetic particles (Mp) include at least one which is the result of a reaction with at least one compound selected from the group consisting of divinylsulfone, benzoquinone, imidazole, periodate, trichloro-S-triazine, tosylates, diazonium, isourea salts, carbodiimides, hydrazine, epichlorohydrin, glutaraldehyde, cyanogenbromide, bisepoxiranes, carbonyldiimidazole, N-hydroxysuccinimide, silanes and derivatives thereof.

In one embodiment the molecules adapted for molecular interactions are introduced on either the porous particles (Pp), the magnetic particles (Mp), or on both.

In one embodiment the molecule adapted for molecular interaction is at least one selected from the group consisting of an organic molecule, a protein, an antigen, an enzyme, an enzyme inhibitor, a cofactor, a hormone, a toxin, a vitamin, a glycoconjugate, a nucleic acid, a lectin, and a carbohydrate.

In one embodiment the magnetic particles (Mp) comprise particles of at least one magnetic material embedded in a polymer matrix, and wherein said polymer matrix comprises the functional groups.

According to one embodiment the magnetic particles (Mp) comprise at least one magnetic material chosen from magnetic metals, magnetic metal alloys and magnetic oxides or combinations thereof. Non-limiting examples include iron, nickel, cobalt, gadolinium, neodymium and samarium, as well as oxides and alloys thereof. In an alternative embodiment the magnetic particles (Mp) comprise at least one magnetic material chosen from iron, nickel, cobalt and oxides and alloys thereof. In another embodiment the magnetic particles (Mp) comprise at least one magnetic material chosen from iron, nickel, cobalt, gadolinium, neodymium and samarium and oxides and alloys thereof.

In one embodiment the magnetic particles (Mp) have a density which is higher than the density of the non-magnetic porous particle (Pp). Thus the magnetic particles (Mp) can be used to increase the density of the entire particles (P). This can be useful if gravity or centrifugation should be used for separating the particles (Sp) during any process.

In a second aspect there is provided a particle (P) comprising a non-magnetic porous particle (Pp) having an exterior surface, pores and an interior surface defined by said pores, the porous particles (Pp) comprising at least one polymer, said particle (Pp) having at least one magnetic particle (Mp) covalently bound thereto, wherein the smallest diameter of at least 95 wt % of all magnetic particles (Mp) is larger than the average diameter of the pores of the porous particles (Pp).

In one embodiment of the second aspect the smallest diameter of at least 95 wt % of all magnetic particles (Mp) is larger than the largest diameter of at least 95% of all pores of the porous particles (Pp).

In one embodiment of the second aspect the porous particle (Pp) comprises at least one material selected from the group consisting of agarose, silica, cellulose, polyvinyl alcohols, polyethylene glycols, polystyrene, dextran, acrylates and derivatives thereof.

In one embodiment the diameter of the porous particles (Pp) is in the range 40-150 μm. In an alternative embodiment the diameter of the porous particles (Pp) is in the range 10-250 μm. For non-spherical particles the diameter is defined as the largest diameter. In one embodiment the size distribution of the sizes of the porous particles (Pp) is narrow so that more than 95 wt % of all particles is within a diameter range so that the upper and lower limit of that range does not differ more than 10%.

In one embodiment of the second aspect the magnetic particles (Mp) have a density which is higher than the density of the non-magnetic porous particle (Pp).

In one embodiment the magnetic particle (Mp) comprise at least one selected from iron oxide and cobalt. In one embodiment the magnetic particle (Mp) comprise a FeCo alloy.

In one embodiment of the second aspect at least one selected from the group consisting of the porous particle (Pp) and the at least one magnetic particle (Mp) comprise molecules adapted for molecular interactions.

In one embodiment of the second aspect the magnetic particles (Mp) comprise particles of at least one material embedded in a polymer matrix, and wherein said polymer matrix comprises the functional groups.

In one embodiment of the second aspect the magnetic particles (Mp) comprise at least one polymer.

The chemical groups on the magnetic particles (Mp) and on the non-magnetic porous particles (Pp) are adapted so that a reaction can occur between chemical groups on the magnetic particles (Mp) and chemical groups on the non-magnetic porous particles (Pp). Thus one functional group which is suitable for reaction with another functional group can be attached to the non-magnetic porous particle (Pp) and a suitable corresponding functional group can be attached to the magnetic particles (Mp). One functional group can be attached either to the non-magnetic porous particle (Pp) or to the magnetic particles (Mp) as long as there is a suitable functional group on the other particle with which it can react. In one embodiment different several chemical groups are attached to the non-magnetic porous particle (Pp) and different types of magnetic particles with corresponding different types suitable functional groups are attached to the different functional groups on the porous particle (Pp).

One way of attaching molecules on the particles (P) is the method described in U.S. Pat. No. 5,942,463.

In one embodiment of the first aspect molecules adapted for molecular interactions are introduced on at least one selected from the group consisting of the porous particles (Pp) and the magnetic particles (Mp). In one embodiment of the first aspect the molecules adapted for molecular interaction is at least one selected from the group consisting of an organic molecule, a protein, an antigen, an enzyme, an enzyme inhibitor, a cofactor, a hormone, a toxin, a vitamin, a glycoconjugate, a nucleic acid, a lectin, and a carbohydrate.

In one embodiment of the first aspect molecules adapted for detection are introduced on at least one selected from the group consisting of the porous particles (Pp) and the magnetic particles (Mp). In one embodiment of the first aspect the molecules adapted for detection is at least one selected from the group consisting of an organic molecule, a protein, a nucleic acid and a lectin.

In one embodiment of the first aspect the magnetic particles (Mp) comprise particles of at least one magnetic material embedded in a polymer matrix, and wherein said polymer matrix comprises the functional groups.

In one embodiment of the second aspect the porous particle (Pp) comprises at least one selected from the group consisting of agarose, silica, cellulose, polyvinyl alcohols, polyethyleneglycols, polystyrene, and derivatives thereof.

The magnetic particles (Mp) comprise at least one magnetic material, for example but not limited to magnetic metals, magnetic metal alloys, and magnetic oxides or combinations thereof.

In one embodiment the magnetic particles (Mp) have a density which is higher than the density of the non-magnetic porous particle (Pp). The density is measured according to ISO 1183-1:2012.

In one embodiment at least one of the porous particle (Pp) and the at least one magnetic particle (Mp) comprise molecules adapted for molecular interactions. A molecule adapted for interaction is a molecule with the ability to interact with another molecule by means including but not limited to forming a bond with another molecule.

In one embodiment at least one of the porous particle (Pp) and/or the at least one magnetic particle (Mp) comprise molecules adapted for detection.

In one embodiment the molecules adapted for detection is at least one selected from the group consisting of an organic molecules, a nucleic acid, an antigen, an enzyme, an enzyme inhibitor, a cofactor, a hormone, a toxin, a glycoconjugate, a lectin, and a carbohydrate. A molecule adapted for detection is a molecule which can be detected by any means. Examples include molecules which irradiate light of at least one specific wavelength.

In one embodiment the magnetic particles (Mp) comprise particles of at least one material embedded in a polymer matrix, and wherein said polymer matrix comprises the functional groups. Examples of materials in the magnetic particles (Mp) include but are not limited to magnetic metals, magnetic metal alloys, and magnetic oxides, such as iron, cobalt, and oxides thereof.

In one embodiment the porous particle (Pp) is much larger than the magnetic particle (Mp), in one embodiment the porous particle (Pp) is at least 5, preferably at least 10 times than the magnetic particle (Mp) referring to the size. For non-spherical particles the smallest diameter is used.

According to one embodiment the particle (P) is a chromatographic separation medium. In a column for chromatography the chromatographic medium comprises a large number of particles (P) and can be utilized as conventional chromatographic medium.

Herein is also provided a method for performing an assay comprising use of particles (P) as described in the second aspect, said method comprising the steps of: a) contacting the particles (P) with at least one analyte to be analysed, b) exposing the particles (P) to at least one selected from the group consisting of i) a magnetic field, ii) gravity, and iii) centrifugation, and c) reading a detectable signal from the particles (P).

Separation can be performed by both a magnetic field or by using a difference in density. In one embodiment the magnetic particles are magnetic and have high density so that a separation based on a magnetic field and/or a separation based on a density difference can be used. A separation based on density includes centrifugation and/or exposure to gravity. Exposure to gravity is simply to let the sample stand so that denser particles settle.

EXAMPLES

Example 1

Preparation of Epoxide-Activated Agarose Particles

Agarose 6B, agarose CL 6B, agarose 4B and agarose CL 4B were separately activated with epoxide groups as follows. The agarose gels were washed with distilled water on a glass filter and sucked dry. Approximately 3 g dry agarose gel particles were suspended in 2.4 ml 1M sodium hydroxide solution and epichlorohydrin 0.45 ml was added drop wise under stirring at room temperature. The temperature was increased to 60° C. and maintained for 2 hours. The epoxide-activated agarose gels were washed with distilled water until neutral on a sintered filter funnel (Por 3) and finally re-suspended in distilled water, 50% gel concentration. The products constitute an example of porous particles (Pp). The average apparent pore radius is about 24-45 nm.

Example 2

Covalent Immobilization of Magnetic Particles on the Outer Part of Epoxide-Activated Agarose Particles Commercially available magnetic nano- and microparticles with amino ($NH_2$) functionality in the sizes from 30 nm to 10 μm were used in these investigations as the magnetic material. These particles are examples of magnetic particles (Mp).

The magnetic particles (Mp) were typically covalently attached to the porous epoxide-activated agarose particles (Pp) as follows. Thiolated Micromer® —M-$NH_2$ (250 μL, $7 \times 10^8$ particles/ml), from Micromod Partikelteknologie GmbH, was washed two times with 1000 μL PBS (15 mM phosphate, 150 mM NaCl, pH 7.4) and re-suspended in 1000 μL PBS. The epoxide-activated agarose particles, 1 ml settled gel, were re-suspended in 10 ml 0.01 M NaOH solution, added to the magnetic particle suspension and reacted for 12 hours at room temperature on vortex.

Figure 1:
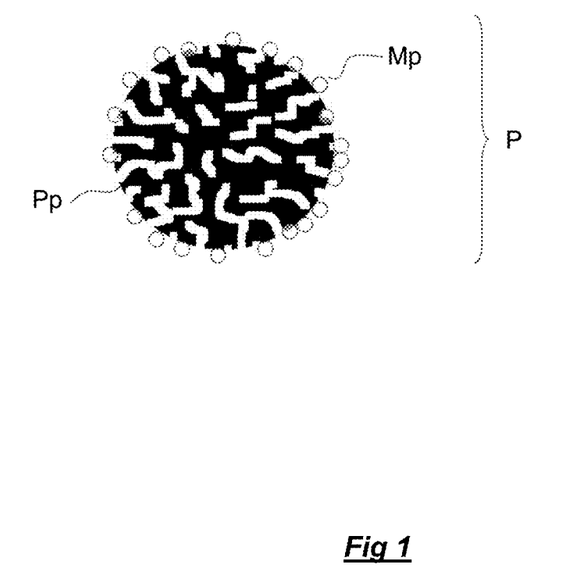
FIG. 1 schematically shows a cross-section of a particle (P) comprising a porous non-magnetic particle (Pp) and multiple magnetic particles (Mp) distributed over its surface. In this particular embodiment the magnetic particles (Mp) are not attached to the interior surface of the porous particle (Pp), but instead to the exterior surface of the porous particle (Pp).
Figure 2:
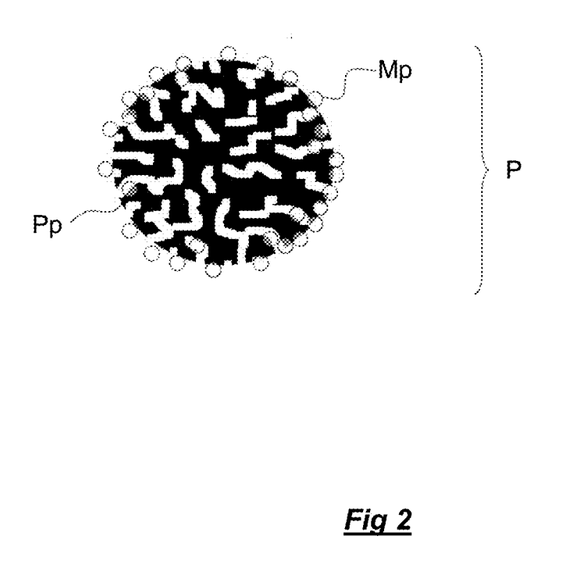
FIG. 2 schematically shows the cross-section of a similar particle (P) comprising a non-magnetic porous particle (Pp) with magnetic particles (Mp) which, depending on their size in relation to the diameter of the pores in the porous particle, have penetrated to a lesser or greater extent into said particle. In this particular embodiment the magnetic particles (Mp) are thus attached to both the interior surface and the exterior surface of the porous particle (Pp).
Figure 3:
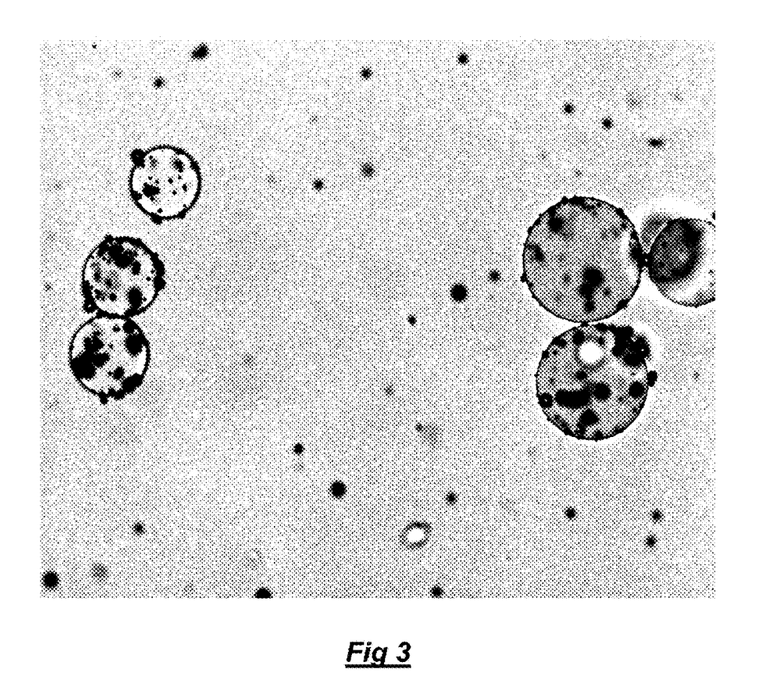
FIG. 3 shows an optical microscope image of agarose beads as porous particles with smaller magnetic particles bound to their surface, resulting from a reaction between epoxide-activated agarose 6B and thiolated Micromer® M $NH_2$ particles having the sizes 10 μm, 5 μm and 2 μm.
Figure 4:
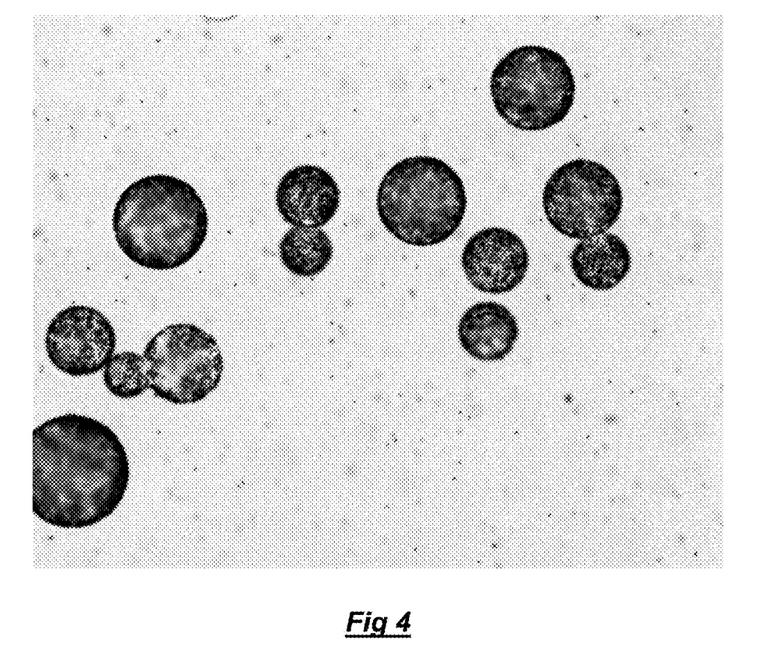
FIG. 4 shows an optical microscope image of magnetic agarose particles resulting from the reaction between epoxide-activated agarose 6B and 2 μm Micromer® M $NH_2$ particles.

Excess magnetic particles with amino functionality were removed on a sintered filter funnel with 50 ml 10 mM sodium phosphate buffer pH 7.4 resulting in a solution with agarose particles decorated with magnetic particles, FIG. 3 and FIG. 4 showing agarose 6B particles decorated with magnetic particles. This would constitute the particles (P).

Example 3

Magnetic Separation of the Magnetic Particles (P)

Figure 5:
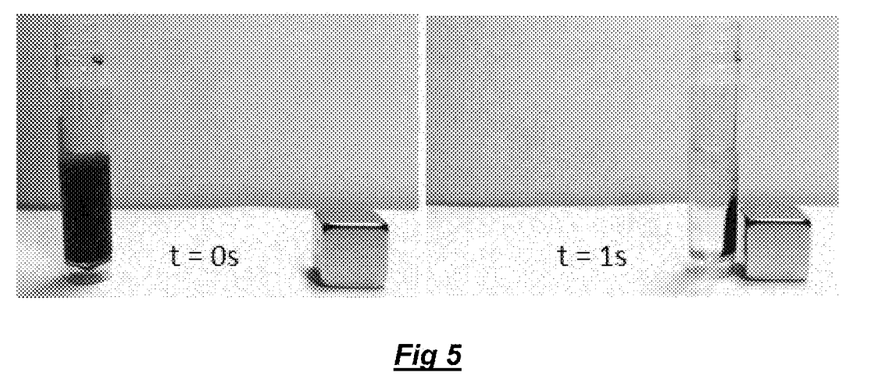
FIG. 5 shows an image of the separation of magnetic agarose 4B particles by using a permanent cube magnet.

Approximately 50 μl settled magnetic particles (P) suspended in 1000 μl PBS were transferred to 2 ml vials. The vials were vortexed and exposed to a permanent cube magnet for 5 seconds. Within 1 second the magnetic agarose 6B, CL 6B, 4B and CL 4B particles were completely adhered to the wall of the vial adjacent to the permanent cube magnet. The magnetic separation is illustrated in FIG. 5 for the magnetic agarose 4B particles.

Example 4

Immobilization of Thiolated Protein A to Magnetic Agarose Particles

Approximately 60 μl of settled magnetic agarose 6B, CL 6B, 4B and CL 4B particles were pipetted to a 1.5 ml Eppendorf tube. The magnetic agarose particles were attracted to the wall of the Eppendorf tube by a permanent magnet and the solution was removed and the particles were re-suspended in 1 ml solution of thiolated protein A (1 mg/ml in 15 mM phosphate buffer pH 8). After 1 hour reaction at room temperature and by gentle mixing the supernatant was collected by separation of the particles from the solution by a permanent magnet. The content of protein A in the supernatant was evaluated with Uv/Vis spectroscopy by measuring the absorbance at 280 nm (A280 nm), see Table 1 for the reaction with magnetic agarose 4B particles.

TABLE 1

Evaluation of the ligand concentration of protein A on to magnetic agarose 4B particles by measuring the absorbance at 280 nm on the supernatant.

| Sample | Absorbance, 280 nm $A_{280\ nm}$ |
|---|---|
| Protein A 0 mg/ml | 0.001 |
| Protein A 0.5 mg/ml | 0.142 |
| Protein A 1.0 mg/ml | 0.274 |
| Supernatant, Protein A + magnetic agarose 4B particles | 0.166 |

The content of protein A on the 60 μl magnetic agarose 4B particles was determined by subtracting the content of protein A in the supernatant (0.6 mg/ml) from the content in the added protein A solution (1 mg/ml). The ligand concentration of protein A was determined to be around 6.5 mg/ml settled magnetic agarose 4B particles.

Example 5

Capture of Human IgG with Protein A Magnetic Agarose Particles

Approximately 50 μl of settled protein A magnetic agarose 6B, CL 6B, 4B and CL 4B particles in 0.5 ml PBS were transferred to 2 ml vials and further washed 2 times with 1.0 ml PBS by the use of a magnet to remove any unbound protein A and storage solution. The protein A magnetic agarose particles were re-suspended in 1.0 ml solution of human IgG (2 mg/ml) and reacted for 60 minutes at room temperature and with end-over-end mixing. The supernatant was then collected by separation of the particles from the solution with a permanent magnet and stored for IgG quantification (IgG binding capacity) with Uv/Vis spectroscopy at 280 nm. The magnetic agarose particles were then washed two times with 1.0 ml PBS in order to remove unbound proteins and impurities. The protein A captured human IgG were then eluted from the magnetic agarose particles by addition of 500 µl citrate solution (60 mM, pH 3.0). After 15 minutes vortexing at room temperature the elution fractions were collected, diluted with 500 µl PBS and stored for IgG quantification (recovery) with Uv/Vis spectroscopy at 280 nm, see Table 2. The absorbance for human IgG at 280 nm was set to be 1.38 at 1.0 mg/ml.

TABLE 2

IgG binding capacity and recovery for the protein A magnetic agarose particles.

| Protein A magnetic agarose particles | IgG binding capacity (mg) | Recovery (%) |
|---|---|---|
| Agarose 6B | 0.9 | 80 |
| Agarose CL 6B | 0.8 | 82 |
| Agarose 4B | 1.7 | 85 |
| Agarose CL 4B | 1.5 | 79 |

The capacities per ml magnetic particles to bind human IgG were determined to be approximately:
- 18 mg/ml settled protein A magnetic agarose 6B particles
- 16 mg/ml settled protein A magnetic agarose CL 6B particles
- 34 mg/ml settled protein A magnetic agarose 4B particles
- 30 mg/ml settled protein A magnetic agarose CL 4B particles To the best of the authors knowledge, the IgG binding capacities for the protein A magnetic agarose 4B and CL 4B are the highest available for any kind of magnetic particle.

Example 6

Primary Purification of IgG from Human Serum with Protein A Magnetic Agarose Particles The purification of IgG from human serum with protein A magnetic agarose 6B and 4B particles was compared with the conventional solid magnetic particle Dynabeads® protein A. 500 µl of 10% protein A magnetic agarose 6B and 4B particle solutions (50 µl particles) and 500 µl Dynabeads® protein A solution were tested in parallel as described below. 500 µl of Protein A magnetic particles were added to 1.5 ml micro centrifuge tubes. The storage solution was removed by means of magnetic separation. The magnetic particles were washed with 1 ml of PBS. The suspension was removed by magnetic separation. The magnetic particles were re-suspended in 500 µl of PBS.

350 µl of human serum was added to the microcentrifuge tubes containing 500 µl of magnetic particle suspension and the mixtures were mixed gently for 60 minutes at room temperature in order to allow capture of IgG to the protein A magnetic particles.

The particles were washed three times with 1 ml PBS using magnetic separation in order to remove unbound proteins and impurities.

Figure 6:
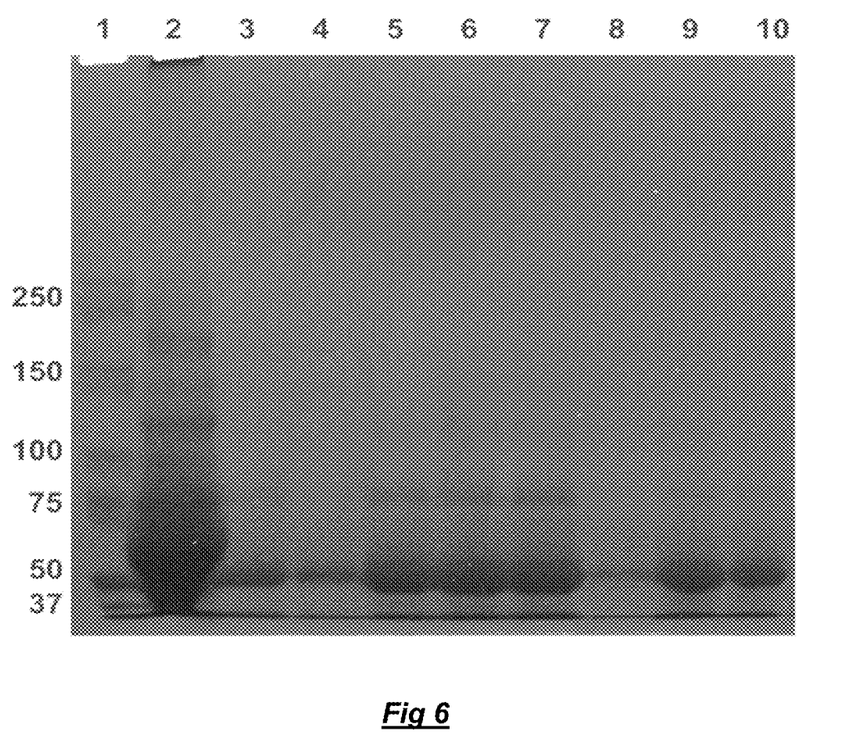
FIG. 6 shows an image of SDS-PAGE gel under reducing conditions for the purification of IgG from human serum with protein A functionalized magnetic agarose 4B and 6B particles and Dynabeads®. Lane 1: Protein molecular weight marker; Lane 2: Human serum before purification; Lane 3-4: Elution fraction from protein A magnetic agarose 6B particles; Lane 5-7: Elution fraction from protein A magnetic agarose 4B particles; Lane 8: Elution fraction from protein A Dynabeads®; Lane 9-10: 98% purity human IgG 10 and 20 μg, respectively.

The PBS suspension was removed from particles with magnetic separation. 500 µl of elution buffer (60 mM Citrate, pH 3.0) was added to the particles and the mixtures were mixed for 15 minutes at room temperature in order to allow elution of IgG from protein A magnetic particles. The elution fractions were collected by magnetic separation and neutralized with 70 µl of 1 M Tris-HCl, pH 9.0. The eluates were resolved by Sodium Dodecyl Sulfate—Polyacrylamide Gel Electrophoresis (SDS—PAGE) reducing conditions, see FIG. 6.

results indicate that the protein A magnetic agarose particles (lane 3-7 in FIG. 6) outperformed it's Dynabead® counterpart (lane 8 in FIG. 6) by far in the means of antibody yield. All of the fractions shows high specific purifications compare to 98% pure human IgG (lane 9-10 in FIG. 6) where protein A magnetic agarose 4B (lane 3-5 in FIG. 6) shows higher yield than the protein A magnetic agarose 6B particles (lane 6-7) in concordance with previous results on IgG binding capacities. Approximately 2 mg human IgG was quantified in each elution fraction using the protein A magnetic agarose 4B particles.

The invention claimed is:

1. A method for production of particles (P), said method comprising the steps of:
    a) providing non-magnetic porous particles (Pp) having an exterior surface, pores and a connected interior surface between said pores, wherein the porous particles (Pp) comprise at least one polymer and at least one type of functional group(s) on said exterior and interior surfaces;
    b) determining the average diameter of the pores of the porous particles (Pp);
    c) providing magnetic particles (Mp) comprising at least one type of functional group(s) on the surface and having a size such that the smallest diameter of at least 95 wt % of all magnetic particles (Mp) is larger than the average diameter of the pores of the porous particles (Pp), and wherein a fraction of the magnetic particles (Mp) have such a diameter to enter the porous particles (Pp), and
    d) reacting the functional group(s) on the surface of the non-magnetic porous particle (Pp), with the functional group(s) on the surface of the magnetic particles (Mp) to form a covalent bond, to obtain particles (P) containing the magnetic particles (Mp) covalently bound to at least one type of the functional group(s) on the interior surface and the exterior surface of the porous particles (Pp), wherein not all of the at least one type of functional groups on the surface of the magnetic particles (Mp) have reacted to form covalent bonds with the at least one type of functional groups on the exterior and interior surfaces of the porous particles (Pp) so that a fraction of the at least one type of functional groups remain reactive on at least one of the magnetic particles (Mp) and the porous particles (Pp).

2. The method according to claim 1, wherein the porous particles (Pp) comprise at least one polymer selected from the group consisting of agarose, silica, cellulose, polyvinyl alcohols, polyethylene glycols, polystyrene, dextran, acrylates and derivatives thereof.

3. The method according to claim 1, wherein the magnetic particles (Mp) have a density which is higher than the density of the non-magnetic porous particle (Pp).

4. The method according to claim 1, wherein the at least one type of functional group(s) on the exterior and interior surfaces of the porous particle (Pp) are selected from the group consisting of —SH, —S—S-pyridine, —COOH—, NH$_2$, —CHO, —OH, phenol, anhydride, epoxy, S-Au, and amide.

5. The method according to claim 1, wherein the at least one type of functional group(s) on the exterior and interior surfaces of the porous particle (Pp) comprise at least one group which is the result of a reaction of the at least one polymer with at least one compound selected from the group consisting of divinylsulfone, benzoquinone, imidazole, periodate, trichloro-S-triazine, tosylates, diazonium, isourea salts, carbodiim ides, hydrazine, epichlorohydrin, glutaraldehyde, cyanogenbromide, bisepoxiranes, carbonyldiimidazole, N-hydroxysuccinimide, silanes and derivatives thereof.

6. The method according to claim 1, wherein the at least one type of functional group(s) on the magnetic particles (Mp) are selected from the group consisting of —SH, —S—S-pyridine, —COOH—, $NH_2$, —CHO, —OH, phenol, anhydride, epoxy, S—Au, and amide.

7. The method according to claim 1, wherein the magnetic particles (Mp) comprise at least one polymer.

8. The method according to claim 1, wherein the at least one type of functional group(s) on the surface of the magnetic particles (Mp) comprise at least one group which is the result of a reaction with at least one compound selected from the group consisting of divinylsulfone, benzoquinone, imidazole, periodate, trichloro-S-triazine, tosylates, diazonium, isourea salts, carbodiim ides, hydrazine, epichlorohydrin, glutaraldehyde, cyanogenbromide, bisepoxiranes, carbonyldiimidazole, N-hydroxysuccinimide, silanes and derivatives thereof.

9. The method according to claim 1, wherein the method further comprises introducing other molecules on to at least one of the porous particles (Pp), and the magnetic particles (Mp) for interactions with another molecule.

10. The method according to claim 1, wherein the magnetic particles (Mp) comprise particles of at least one magnetic material embedded in a polymer matrix, and wherein said polymer matrix comprises the at least one type of functional group(s).

11. The method according to claim 1, wherein the unreacted fraction of the at least one type of functional group(s) on the surface of the magnetic particles (Mp) is reacted to facilitate subsequent binding of other molecules to the magnetic particles (Mp).

12. The method according to claim 1, wherein the at least one type of functional group(s) on the exterior and interior surfaces the porous particle (Pp), or the at least one type of functional group(s) on the magnetic particles (Mp) are selected from the group consisting of IDA (Imminodiacetate), TED (tris(carboxymethyl)ethylenediamine), CM-Asp (carboxymetylated aspartic acid), NTA (nitrilotriacetic acid), TREN (tris(2-aminoetyl)amine), DPA (dipicolylamin), C6-S gel (hexylsulfido groups), EDTA (Etylenediaminetetraacetate), and derivatives thereof.

13. The method according to claim 1, wherein the at least one type of functional group(s) on the exterior and interior surfaces of the porous particle (Pp), or the at least one type of functional group(s) on the magnetic particles (Mp) comprises at least one group selected from organic compounds having the formula $C_nH_m$ ($1 \leq n \leq 20$, $4 \leq m \leq 42$), phenol or derivatives thereof, thiophenol and derivatives thereof, or mercaptopyridine and derivatives thereof.

14. The method according to claim 1, wherein the at least one type of functional group(s) on the exterior and interior surfaces of the porous particle (Pp), or the at least one type of functional group(s) on the magnetic particles (Mp) comprises at least one group selected from aminoethyl, diethylaminoethyl, quaternary aminoethyl, carboxymethyl, phosphoryl and sulphopropyl, or derivatives thereof.

15. A particle (P) prepared by the method of claim 1 comprising a non-magnetic porous particle (Pp) having an exterior surface, pores and an interior surface defined by said pores, the porous particles (Pp) comprising at least one polymer, said particle (Pp) having at least one magnetic particle (Mp) covalently bound thereto, wherein the smallest diameter of at least 95 wt % of all magnetic particles (Mp) is larger than the average diameter of the pores of the porous particles (Pp), and wherein a fraction of the magnetic particles (Mp) have a diameter such that enter the porous particles (Pp).

* * * * *